United States Patent [19]

Shields et al.

[11] Patent Number: 5,698,771
[45] Date of Patent: Dec. 16, 1997

[54] VARYING POTENTIAL SILICON CARBIDE GAS SENSOR

[75] Inventors: Virgil B. Shields, Compton; Margaret A. Ryan, Pasadena; Roger M. Williams, Azusa, all of Calif.

[73] Assignee: The United States of America as represented by the United States National Aeronautics and Space Administration, Washington, D.C.

[21] Appl. No.: 413,297

[22] Filed: Mar. 30, 1995

[51] Int. Cl.⁶ .................. G01N 27/12; G01N 27/06; H01L 29/66
[52] U.S. Cl. .................. 73/31.05; 73/23.2; 73/23.31; 422/88; 422/94; 324/609; 324/691; 324/663; 338/34
[58] Field of Search .................. 73/31.05, 23.2, 73/31.06, 23.31, 23.32; 422/88, 94; 324/609, 663, 691, 693; 338/34

[56] References Cited

U.S. PATENT DOCUMENTS

| | | | |
|---|---|---|---|
| 4,007,624 | 2/1977 | Chantry et al. | 73/23 |
| 4,244,918 | 1/1981 | Yasuda et al. | 422/95 |
| 4,324,218 | 4/1982 | Hattori et al. | 123/440 |
| 4,351,182 | 9/1982 | Schmidberger | 73/27 R |
| 4,453,126 | 6/1984 | Volgyesi | 324/61 R |
| 4,706,493 | 11/1987 | Chang et al. | 73/23 |
| 4,931,851 | 6/1990 | Sibbald et al. | 357/25 |
| 5,250,170 | 10/1993 | Yagawara et al. | 204/431 |
| 5,296,196 | 3/1994 | Takeshima | 422/98 |
| 5,298,223 | 3/1994 | Berger et al. | 422/54 |
| 5,431,883 | 7/1995 | Barraud | 422/82.01 |

OTHER PUBLICATIONS

Growth of SiC on silicon in a low pressure vertical reactor, by K. G. Irvine et al., Materials Science and Engineering, B11 (1992).

Gas sensors for high temperature operation based on metal oxide silicon carbide (MOSiC) devices, by A. Arbab et al., Sensors and Actuators B: 15–16, 1993.

Direct observation of porous SiC formed by anodization in HF, by J. S. Shor et al., Appl. Phys. Lett. 62 (22) 31 May 1993.

Prospects for device implementation of wide band gap semiconductors, by J. Mater. Res. 7: 235–52, by J. H. Edgar, 1992.

Aluminium nitride/silicon carbide multilayer heterostructure produced by plasma-assisted, gas-source molecular beam epitaxy, by L. B. Rowland et al., pp. 3333–3335, 1993.

Chemical Sensors for High Temperatures Based on Silicon Carbide, A. Arbab et al., Sensors and Materials 4 (1993).

Thin Film and Device of Diamond, Silicon Carbide and Gallium Nitride, by Robert E. Davis, Physica B, pp. 1–15, 1993.

Primary Examiner—Michael Brock
Assistant Examiner—J. David Wiggins
Attorney, Agent, or Firm—John H. Kusmiss

[57] ABSTRACT

A hydrocarbon gas detection device operates by dissociating or electro-chemically oxidizing hydrocarbons adsorbed to a silicon carbide detection layer. Dissociation or oxidation are driven by a varying potential applied to the detection layer. Different hydrocarbon species undergo reaction at different applied potentials so that the device is able to discriminate among various hydrocarbon species. The device can operate at temperatures between 100° C. and at least 650° C., allowing hydrocarbon detection in hot exhaust gases. The dissociation reaction is detected either as a change in a capacitor or, preferably, as a change of current flow through an FET which incorporates the silicon carbide detection layers. The silicon carbide detection layer can be augmented with a pad of catalytic material which provides a signal without an applied potential. Comparisons between the catalytically produced signal and the varying potential produced signal may further help identify the hydrocarbon present.

27 Claims, 5 Drawing Sheets

FIG. 8

VARYING POTENTIAL SILICON CARBIDE GAS SENSOR

ORGIN OF THE INVENTION

The invention described herein was made in the performance of work under a NASA contract, and is subject to the provisions of Public Law 96-517 (35 U.S.C. §202) in which the Contractor has elected not to retain title.

TECHNICAL FIELD

This invention is in the field of semiconductor sensors and, more specifically, involves the detection of hydrocarbon gases by a semiconductor sensor.

BACKGROUND ART

There is a significant need for a compact, rugged component capable of detecting hydrocarbon gases at relatively high temperatures. Such a device would be useful for monitoring the presence of uncombusted hydrocarbons in the exhaust gases of furnaces, turbines, or internal combustion engines that operate by burning hydrocarbon fuels. When a combustion device fails to completely burn its fuel, there is, of course, significant economic waste as purchased fuel is discarded into the exhaust stream without yielding useable energy. Furthermore, there is often a deposition of soot and other products of partial combustion that may contribute to mechanical wear and failure.

An even more pressing problem posed by incomplete combustion is the significant contribution of unburned hydrocarbons to air pollution. The hydrocarbons expelled with an engine's exhaust react with ozone and oxides of nitrogen to create photochemical smog, that noxious brown pall that is the bane of many highly populated urban areas. Not only does smog have a loathsome appearance, obscuring distant vistas, but it also poses significant health hazards. Children growing up in a polluted atmosphere show distinct respiratory impairment. Adults exposed to smog experience a significantly greater incidence of asthma and other respiratory diseases as well.

It is well recognized that automobiles and other vehicles with internal combustion engines are significant contributors to smog. Consequently, modern autos are equipped with catalytic converters to remove hydrocarbons in the exhaust through oxidation. In addition, modern automobiles employ complex microprocessor-controlled systems to ensure that fuel mixtures burn completely so as to avoid overloading the catalytic converter. However, the absence of an effective hydrocarbon sensor capable of operating in the hot exhaust stream means that the automobile control systems are unable to directly sense the presence of hydrocarbons; therefore, they often err on the side of lean mixtures to avoid excess hydrocarbon emissions, frequently compromising performance in the process.

When a mechanical defect results in excessive hydrocarbon emission, the problem is often not detected until after the catalytic converter is overloaded and damaged. If the control system could directly sense the presence of hydrocarbon gases, the fuel mixture could be constantly adjusted to provide maximum performance without excess hydrocarbon emission. If hydrocarbon emission did become excessive through a mechanical failure, an alarm could be sounded so the car owner could immediately obtain necessary repairs.

Semiconductor gas sensors are already known. There are sensors capable of detecting, for example, carbon monoxide, hydrogen, and oxygen. Many of these sensors are based on semiconductor materials, such as tin dioxide or titanium dioxide, that change electrical resistance upon adsorbing a gas. Thus, the sensors are conductiometric—that is, changing their resistance in a predictable manner upon absorption of a given gas. Generally, these sensors can operate with only one species of adsorbable gas present since, with more than one gas capable of being adsorbed by the sensor, there is no way of knowing which of the several gases is actually present and causing a change in resistance. In theory, a conductiometric hydrocarbon sensor might be created, but discrimination among the large number of different hydrocarbons would pose a significant problem.

It is also known in the art that properly prepared crystalline silicon carbide is useful in the formation of semiconductor devices (see J. H. Edgar, *J. Mater. Res.* 7:235–52 (1992). Silicon carbide is known to have a wider energy band gap than more traditional semiconductors such as silicon. This allows the construction of silicon carbide semiconductor devices which are capable of operating at higher temperatures, i.e., well above 280° C., than are silicon semiconductors. The favorable properties of silicon carbide make it possible to prepare semiconductors such as field effect transistors (FET) from this material. In fact, metal oxide field effect transistors (MOSFET), as well as other devices, have already been prepared using silicon carbide.

Although, prior to the instant invention, no hydrocarbon-sensitive silicon carbide FETs had been developed, there has been some work using metal oxide-silicon carbide capacitors to detect hydrocarbon gases. These capacitors consist of a layer of catalytic metal deposited on an insulator which, in turn, is disposed on a layer of silicon carbide. Some of these experiments are reported in A. Arbab, S. Spetz, Q. Wahab, M. Willander, and I. Lundström, *Sensors and Materials* 4:173–85 (1993), and A. Arbab, S. Spetz, and I. Lundström, *Sensors and Actuators B* 15/16:19–23 (1993). The devices reported produced only low-level signals, required very high operating temperatures (generally>500° C.), and did not appear capable of discriminating among various hydrocarbons.

STATEMENT OF THE INVENTION

A hydrocarbon gas detection device operates by dissociating or electrochemically oxidizing hydrocarbons adsorbed to a silicon carbide detection layer. Dissociation or oxidation are driven by a varying potential applied to the detection layer. Different hydrocarbon species undergo reaction at different applied potentials so that the device is able to discriminate between various hydrocarbon species. The device can operate at temperatures from 100° C. to over 50° C., allowing hydrocarbon detection in hot exhaust gases. The dissociation reaction is detected either as an electrical change in a metal insulator silicon carbide (MIS) capacitor or, preferably, as a change of current flow through a metal insulator silicon carbide field effect transistor (MISFET) of which the silicon carbide detection layer forms the gate. The silicon carbide detection layer can be augmented with a pad of catalytic material which can provide a signal without an applied potential; in addition, potential can be applied to the catalytic pad to enhance the catalytic reaction. Comparisons between the catalytically-produced signal and the varying potential produced signal further helps identify the hydrocarbon present.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings.

FIG. 7b shows an alternative version of the device of FIG. 7a; and

DETAILED DESCRIPTION OF THE INVENTION

The following description is provided to enable any person skilled in the art to make and use the invention and sets forth the best modes contemplated by the inventors of carrying out their invention. Various modifications, however, will remain readily apparent to those skilled in the art, since the generic principles of the present invention have been defined herein specifically to provide a hydrocarbon gas sensor comprising a sensing element of porous or polycrystalline silicon carbide across which is applied an electrical potential, the potential dissociating adsorbed hydrocarbon molecules allowing the dissociation products to be detected electronically.

It has been discovered that various hydrocarbon gases, such as those likely to be found in the exhaust of an automobile, can become adsorbed to silicon carbide surfaces. The exact physical basis of this adsorption is still being studied;. it may represent an electrostatic attraction or may have some similarity to hydrogen bonding where the relatively electropositive hydrogen atoms of the hydrocarbon interact with the relatively less electropositive carbon atoms of the silicon carbide.

The present invention is based on the discovery that a relatively small electrical potential applied to a silicon carbide structure to which hydrocarbons have become adsorbed results in either electrochemical reaction or dissociation (breaking of carbon-hydrogen bonds) of the hydrocarbon molecule. These reactions release ions so that a sensor that operates amperometrically (current measuring) rather than conductiometrically can be constructed.

In the case of an electrochemical reaction, hydrocarbons adsorb to a silicon carbide surface by electrostatic attraction. If an adequate electrical potential is applied to the silicon carbide, adsorbed hydrocarbons will participate in an oxidation-reduction reaction. That is, the hydrocarbons give up electrons and become oxidized. These electrons are generally captured by oxygen bound to the silicon carbide or to oxygen from water that is also bound to the silicon carbide. Either the oxidizing or the reducing species or the silicon carbide itself act as electrolytes, with the reaction resulting in a net gain of negative charges (hydroxyl ions, oxygen radicals). The oxidation potentials of hydrocarbons vary from about 0.3 V (versus a $H/H_2$ electrode) to between 2 V and 3 V (versus a $H/H_2$ electrode) with larger molecules generally having a lower potential. Thus, if the potential applied to the silicon carbide is varied, the level of potential at which a current, due to the electrochemical reaction, is detected will correspond to the species of hydrocarbon, while the magnitude of the current will correspond to the quantity of the particular species of hydrocarbon.

Detection of hydrocarbons with silicon carbide may also occur through dissociation or covalent bond breakage. Carbon-hydrogen bonds in adsorbed hydrocarbons are broken as the varying applied potential becomes equal to the bond energy of the given carbon-hydrogen bond. This bond breakage will release positively charged hydrogen ions. Generally, smaller alkanes tend to have higher bond strengths than do the larger, more complex hydrocarbons. An average carbon-hydrogen bond will have a strength of about 400 kJ/mole or about 6 eV. This means that most bonds would be expected to break in the 2 to 10 V range of applied potential. As in the case of the electrochemical process, partictilar bonds will break at a different potentials so that the applied potential can be used to identify the particular species of hydrocarbon. Again, magnitude of current produced is a measure of quantity of hydrocarbon present.

The end effect is similar regardless of whether the mechanism is electro-chemical or dissociational. However, electrochemical dissociation occurs at a lower potential than bond dissociation and results in an increase of negative charge as opposed to an increase in positive charge for bond dissociation. The net change in charge caused by the varying potential-induced processes can control the flow of current through the channel of the silicon carbide MISFET either through enhancement or depletion, depending on the precise configuration of the FET design chosen.

Depending on the exact characteristics of the measured gas (i.e., the presence of oxygen or water) and the magnitude of the applied varying potential (0 to about 2 V versus 2 to about 10 V), either or both electrochemical oxidation and bond dissociation can occur on the same sensor. In practice, the varying potential is varied continuously (swept) at a constant rate from 0 to over 10 V to cover the entire range. The actual potential at which a signal is observed will indicate which process is occurring and which type of hydrocarbon is involved. Further, depending on the configuration of the MISFET (i.e., p-type or n-type, depletion mode, or enhancement mode) each process will either increase or decrease current flow through the transistor, with the two processes., having opposite effects because electrochemistry yields negative ions, while dissociation yields positive ions.

Figure 1:
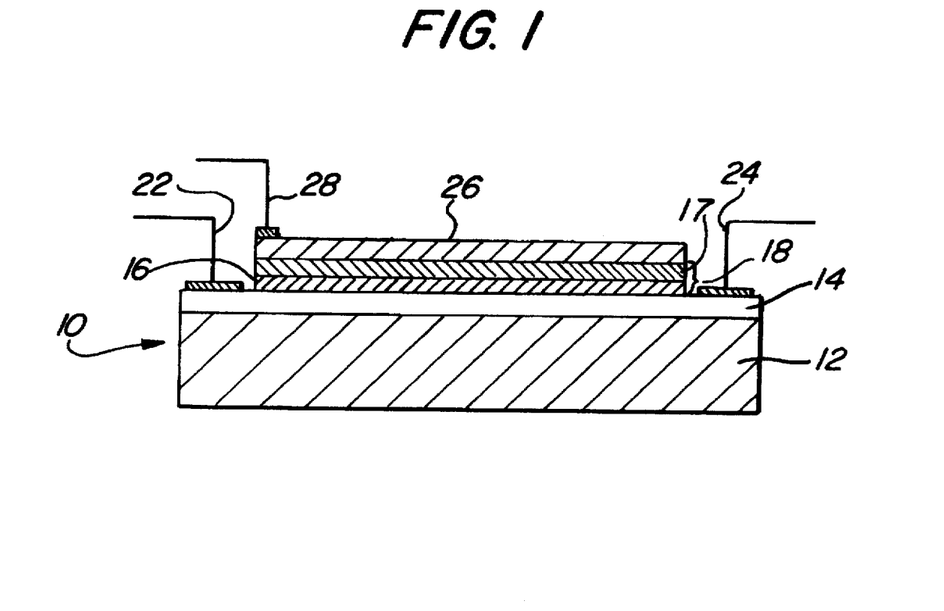
FIG. 1 shows a diagrammatic cross-section of a MISFET of the present invention employing a polycrystalline silicon carbide gate.
Figure 2:
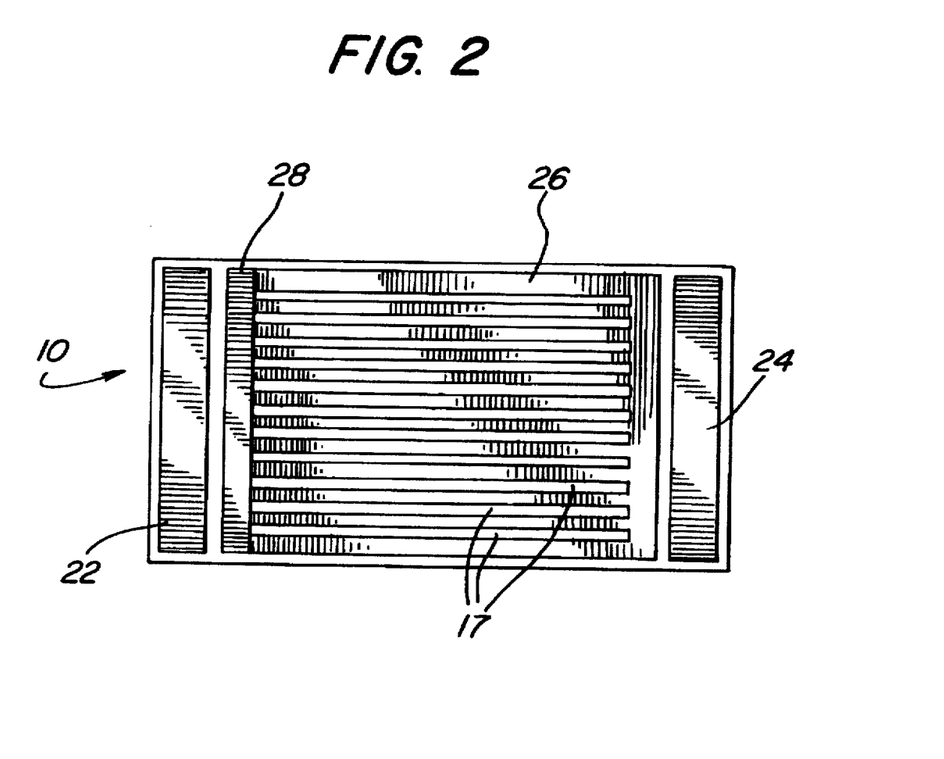
FIG. 2 shows a top view of the device of FIG. 1.

FIG. 1 shows a cross-section of a diagram of one configuration of a sensor 10 of the present invention; FIG. 2 shows a top view of the same device. As will be explained below, various fabrication constraints may result in other configurations being preferred. In the basic design of FIG. 1, a wafer of undoped single crystal silicon carbide 12 forms a substrate on which the device is formed using conventional methods of semiconductor fabrication such as Chemical Vapor Deposition (CVD) to deposit additional layers (see K. G. Irvine, I. Jenkins, W. Givens, M. G. Spenser, M. Aluko, *Mater. Sci. and Engineering* B11:93–96 (1992)).

It is well known in the art that silicon carbide is polytypic, having more than 250 possible crystal structures. In constructing a multilayered semiconductor device, attention must be paid to crystal structures created to ensure that the crystal lattices of the various layers align properly. Two of the silicon carbide crystal types are of particular interest: the cubic (zincblende) or 3C—SiC form and the hexagonal or 6H—SiC form. A MISFET-based sensor 10 is constructed by forming a region of doped (with added impurities) silicon carbide called a current channel 14 and a gate 18 of undoped polycrystalline silicon carbide separated by a thin insulator layer 16. The MISFET operates when an electrical charge in the gate 18 influences the flow of current through the channel 14 form a source electrode 22 to a drain electrode 24.

In the sensor 10 of the present invention the channel 14 is produced by depositing the channel layer 14 of doped silicon carbide onto the silicon carbide substrate wafer 12. The current sensor 10 uses nitrogen doping to form an n-type channel, although other donor dopants such as nickel could also be employed. Because of crystal lattice compatibility, the insulator 16 of choice is aluminum nitride although, again, other insulating materials known to the art, i.e. silicon dioxide, can also be employed. The 2H—AlN crystal form of aluminum nitride has very similar lattice spacing to that of 6H—SiC, allowing single crystal aluminum nitride to be grown on 6H—SiC. The wafer 12 is usually of 6H—SiC to ensure proper orientation and bonding of the 1000–2000 Å thick aluminum nitride insulator 16, although cubic 3C—SiC can also be successfully employed.

In the present invention the gate 18 is also of silicon carbide grown on the aluminum nitride insulator 16 by CVD. To ensure a detectible signal from hydrocarbon adsorbed to the silicon carbide gate 18, it is necessary to provide a larger-surface area on which the gases can adsorb. One method of achieving greater surface area is to create the silicon carbide gate 18 out of a layer of poly-crystalline silicon carbide 17. This material consists of numerous small silicon carbide crystals with significant adsorptive area created by the multiple grain boundaries. A 1000–2000 Å layer 17 of polycrystalline silicon carbide can be produced by growing the silicon carbide at a lower temperature (below 1,100° C.) than is used to deposit single crystal silicon carbide.

Adsorbed hydrocarbons influence the current flow in the channel 14 when they are dissociated or electrochemically oxidized and thereby produce species capable of altering the charge on the gate 18. As explained above, dissociation or electrochemical reaction is accomplished by applying a varying potential across the silicon carbide gate 18. A 2000 Å thick metal grid 26 deposited on top of the polycrystalline silicon carbide layer 17 (see FIG. 2) is attached to a varying potential electrode 28 which introduces the dissociating potential. Because the sensor 10 is intended to be operated at high temperatures (over a range from about 100° C. to at least as high as 650° C.), the grid 26 and electrode 28 are preferentially formed from a metal such as chromium that does not melt, vaporize, or react with silicon carbide at high temperatures. A potential between 0 and about 10 volts is applied to the electrode 28 so that the gate 18 is at the applied potential relative to the channel 14. The varying potential exists between the gate 18 and the channel 14 and drives an electrochemical reaction and/or breaks carbon-hydrogen covalent bonds. The products of the reaction or dissociation alter the charge of the gate 18 and influence current flow in the channel 14.

A sensor as described in FIGS. 1 and 2 can be fabricated as follows. The silicon carbide substrate 12 is first cleaned and prepared, as is usual in the art, to remove all contaminants and stress from the surface so as to permit epitaxial growth. A typical epilayer can be grown on the substrate following methods well known in the art (see, for example, R. Davis, *Physica B* 185:1–15 (1993)). The first epilayer forms the current channel 14 of the device 10. An epilayer of aluminum nitride (see L. B. Rowland, R. S. Kern, S. Tanaka, R. F. Davis, *Appl. Phys. Lett.* 62:3333–35 (1993)) is then grown on top of the silicon carbide channel 14 followed by a polycrystalline layer 17 of silicon carbide grown in the same reaction chamber to prevent contamination. The exposed surfaces of the device 10 are protected by passivation using thermal oxidation in dry oxygen for about 30 minutes at 1100° C. The oxide is removed from the polycrystalline silicon carbide layer 17 and from the contact areas for the source electrode 22 and the drain electrode 24 using hydrofluoric acid. Chromium to form the metal grid 26 and the varying potential 28, the source 22 and the drain 24 electrodes is then vacuum evaporated onto the device 10 typically at $1 \times 10^{-6}$ to $1 \times 10^{-7}$ torr.

As reported in J. S. Shor, I. Grimberg, B. Weiss and A. D. Kurtz, *Appl. Phys. Lett.* 62:2836–2838 (1993), it is possible to create porous silicon carbide by an etching process which creates pores oriented along the C-axis of hexagonal or 6H—SiC. Porous silicon carbide is ideal if the pores are oriented perpendicularly to the top surface of the structure so that a large number of pore openings are exposed for the hydrocarbon gases to enter, thereby providing a large surface area for gas adsorption. However, the process of etching silicon carbide imposes certain limitations on the configuration of the resulting device.

The silicon carbide is etched through a photoelectrochemical anodization process. The silicon carbide must be attached to an electrical conductor on one surface, while the opposite surface is exposed to a strong (about 300 mW/cm²) beam of ultraviolet (250–400 nm) light in a dilute hydrofluoric acid bath. It is not possible to readily apply this process to the silicon carbide gate 18 as configured in FIGS. 1 and 2. Therefore, one must employ a different fabrication scheme which starts with a silicon carbide wafer and converts that wafer into a porous gate.

Figure 3:
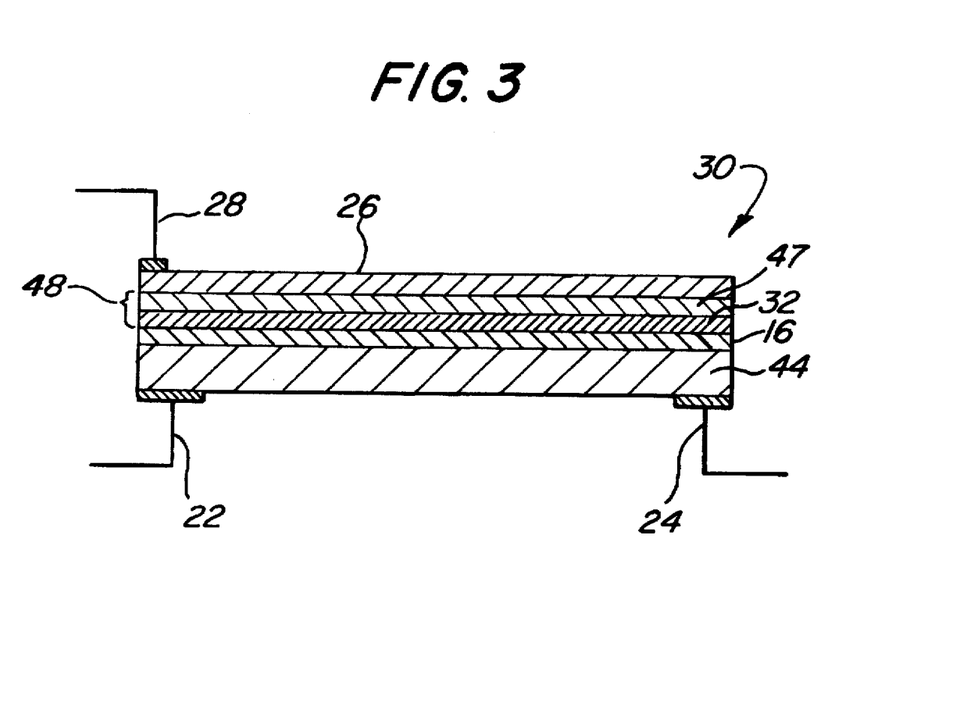
FIG. 3 shows a diagrammatic cross-section of a MISFET of the present invention employing a porous silicon carbide gate.
Figure 4:
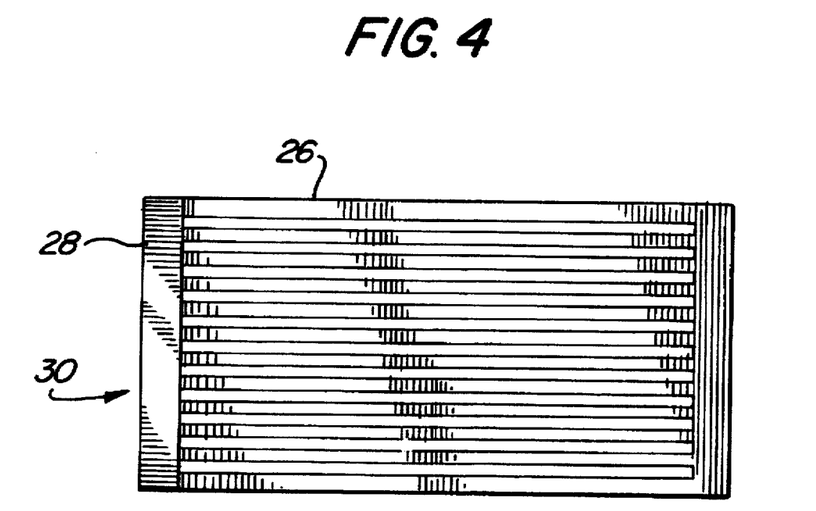
FIG. 4 shows a top view of the device of FIG. 3.

FIG. 3 shows a cross-section of a sensor 30 constructed to permit the use a porous etched silicon carbide current gate 48. The porous gate 48 is topped by a metal grid 26 and varying potential electrode 28 just as in the sensor 10 shown in FIGS. 1 and 2. A porous layer 47 is opposite the aluminum nitride insulator 16 so that the porous silicon carbide layer 47 is sandwiched between the grid 26 and the insulator 16. A doped silicon carbide channel 44 covers the insulator 16. Source 22 and drain 24 electrodes are deposited onto the channel 44.

The structural differences between the polycrystalline sensor 10 and the porous layer gate sensor 30 are a result of the requirement for a backing conductor during the photoelectrochemical etching process. Manufacture of the porous gate sensor 30 starts with a thin wafer 32 of hexagonal silicon carbide cut so that the C-axis is normal to the wafers planar surfaces. A metal electrode (not illustrated) is deposited on one surface of the wafer and the wafer is photoelectrochemically etched so that 10–100 nm pores are formed on the planar surface opposite from the electrode. This leaves a top surface of the wafer 32 transformed into the porous silicon layer 47 which forms the porous layer gate 48.

Generally an undoped wafer 32 about 200–500 μm thickness is used and a porous layer 47 one to a few micrometers thick is etched into the wafer 32. Thus, much of the unetched wafer 32 remains. While the undoped wafer acts as an n-type semiconductor due to atmospheric nitrogen contaminants incorporated during manufacture, the porous etched silicon carbide layer 47 has very high resistivity.

The backing metal electrode is then removed chemically and the aluminum nitride insulator 16 is deposited in its place. A layer of n-type doped silicon carbide is then grown on the surface of the insulator 16 to constitute the channel 44. The metal grid 26 and the varying potential electrode 28 are deposited onto the porous surface 47 of the porous silicon carbide gate 48. The sensor 30 is completed by depositing the source 22 and drain 24 electrodes onto the channel 44. These fabrication steps are the same as those explained above for FIGS. 1 and 2. Those of ordinary skill in the art will appreciate that the passivation step is important to protect the device.

Thus, the porous gate sensor 30 is not formed by growing various layers onto a silicon carbide wafer 12 as is the case with the polycrystalline gate sensor 10. Rather, a silicon carbide wafer 32 is etched to form the porous silicon gate 48 and the remaining layers of the device are then grown onto the gate 48. The major difference visible in the final device is the absence of the silicon carbide wafer 12 backing the channel 44. The polycrystalline silicon carbide gate device 10 shows the metal grid 26 on one surface and the silicon wafer 12 on the opposite surface. The porous gate device 30 grown according to this method shows the metal grid 26 on one surface and the channel 44 with electrodes 22 and 24 on the opposite surface.

Both the polycrystalline gate MISFET 10 and the porous gate MISFET 30 have been illustrated as depletion mode devices. As is well known in the art, these devices can readily be constructed as enhancement mode MISFETs. The invention lies in the employment of a porous or polycrystalline silicon carbide gate to which a varying potential is applied to produce electrochemical oxidation or dissociation of adsorbed hydrocarbons.

Figure 5A:
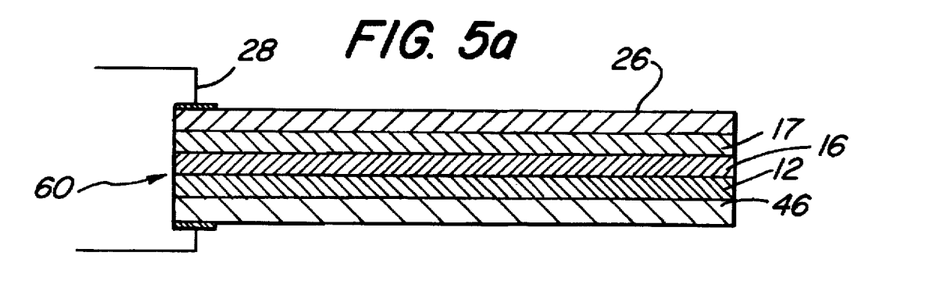
FIG. 5a shows a diagrammatic cross-section of a MIS capacitor with a poly-crystalline silicon carbide layer.

In carrying out experiments to test various parameters of the polycrystalline or porous silicon carbide sensor 10, 30, there are considerable advantages in cost and time to testing the porous silicon carbide or polycrystalline silicon carbide alone as opposed to constructing entire MISFETs. FIG. 5a shows a device 60 fabricated to test an individual polycrystalline layer 17; the polycrystalline silicon carbide layer 17 is deposited on the insulator 16 which, in turn, has been deposited directly onto the silicon carbide wafer 12, the metal grid 26, and the varying potential electrode 28 are then deposited onto the polycrystalline silicon carbide 17. The back electrode 46 is added to complete the device 60. It has been found that polycrystalline silicon carbide may be excessively conductive due to grain boundary conduction. This problem can be controlled by slightly doping the poly-crystalline silicon carbide with an electron acceptor such as boron.

Figure 5B:
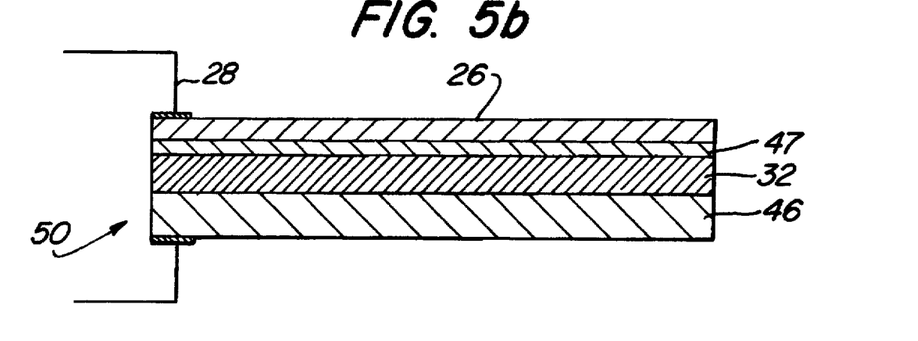
FIG. 5b shows a diagrammatic cross-section of a MIS capacitor with a porous silicon carbide layer.

FIG. 5b shows a device 50 fabricated to test an individual porous silicon carbide layer 47; the silicon carbide wafer 32 is equipped with a back electrode 46 for the photoelectrochemical etching process as explained above. After the etching is complete, the open metal grid 26 and the varying potential electrode 28 are deposited on the porous surface 47.

The described test structures, FIGS. 5a, 5b, comprise sandwiches of two electrodes (the back electrode 46 and the metal grid 26) with other layers between. These devices act as MIS capacitors 60, 50 whose electrical characteristics are altered by the presence of hydrocarbons adsorbed to the polycrystalline silicon carbide layer 17 and the porous silicon carbide layer 17, respectively, when adsorbed hydrocarbons are dissociated by the applied varying potential.

Figure 6:
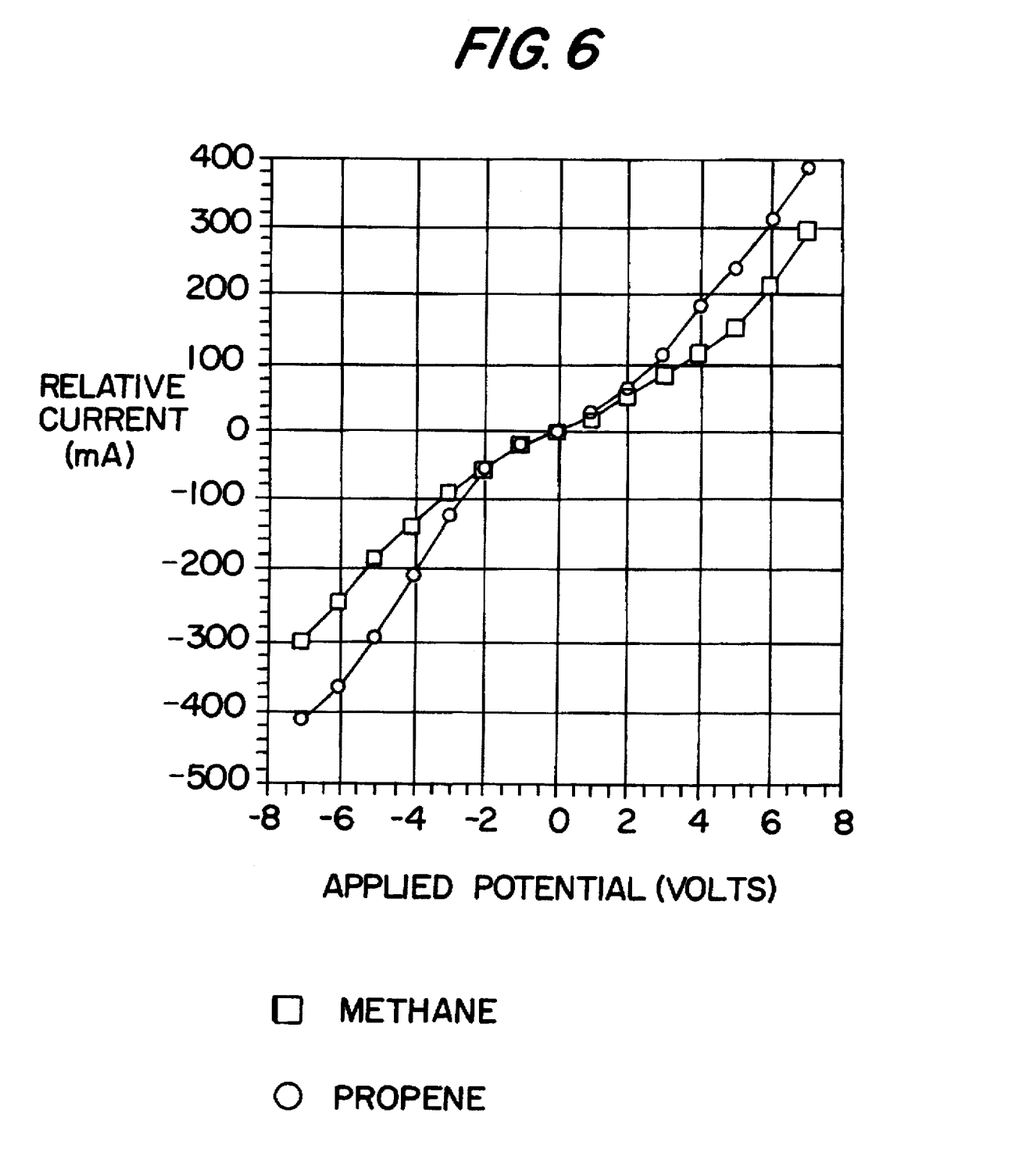
FIG. 6 shows the electrical response of the device of FIG. 5b to hydrocarbon gases.

FIG. 6 shows typical results of testing the porous silicon carbide capacitor 50. A flow of current (Relative Current) is measured across the electrodes 28 and 46 as the applied potential is varied between −8 V and +8 V at a temperature of 223° C. This temperature is considerably lower than that reported for gas detecting capacitors based on catalytic materials. A first trace represents the current produced by methane, the smallest alkane. A second trace shows the current produced by propene, a three carbon alkene. Both traces are shown relative to the current produced by the sensor 50 in an atmosphere of inert argon, to zero out any current leakage in the capacitor. The difference in shape between the traces produced by the two different hydrocarbons reflects the differences in bond energy between propene and methane showing that the device can discriminate between different hydrocarbons.

One problem that may affect the performance of the sensors of the present invention is excess accumulation of reaction products or "fouling" of the detection layer by adsorbed hydrocarbons or impurities. It has been found that reversing the polarity of the varying potential and increasing its magnitude often results in expulsion of at least some of the excess accumulation, thus regenerating the detection layer. Care must be taken not to use so high a potential as to puncture the thin insulator 16. In most cases a potential of 100 V or so can be safely, tolerated. In many cases the devices of the present invention will be fabricated with integral zener diodes to protect the insulator 16 as is common in many MOSFETs. If potential reversal is not adequate to regenerate the device, mechanical cleaning such as by ultrasound may be necessary.

Figure 7A:
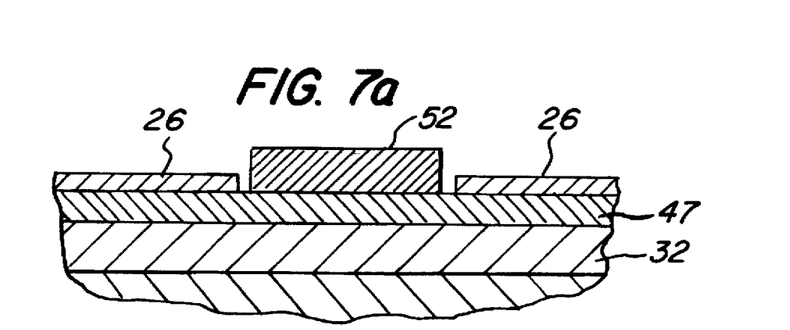
FIG. 7a shows a porous silicon carbide layer with a catalytic pad.
Figure 7B:
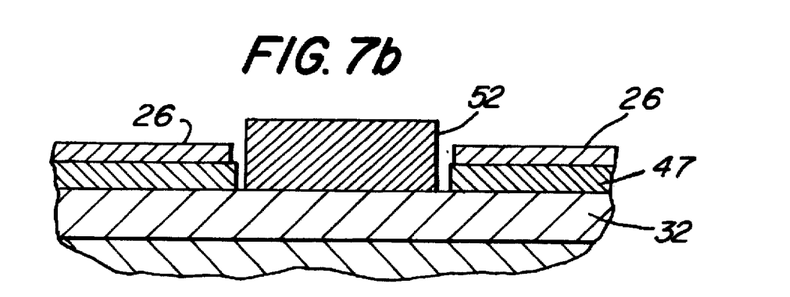

FIGS. 7a–7b shows additional modifications that can be made to the porous silicon carbide layer 47; the modification of FIG. 7a can be made to the polycrystalline silicon carbide layer 17 as well. The modifications can be applied to detection layers of either MISFETs or to MIS capacitors. The figures illustrate only a portion of the detection layer. The variable potential electrode 28-as well as other layers of a functioning device are not illustrated.

In FIG. 7a a pad 52 (or pads) of a catalytic metal or a catalytic metal compound is deposited over a portion of the polycrystalline or porous silicon carbide layers 47. The pad 52 can be deposited by conventional evaporation techniques in the case of a pure metal or by CVD in the case of metal compounds. The list of usable metals and compounds is long; virtually any material that shows catalytic activities towards hydrocarbons is useful. This includes platinum, vanadium, molybdenum carbide, tungsten carbide, titanium carbide, niobium carbide, and palladium. The pad 52 can be in contact with the metal grid 26 (not illustrated), in which case the applied potential may also augment the catalytic reaction. Alternatively, the pad 52 may be isolated from the grid 26 so that there is no interaction between the applied potential and the pad 52.

The catalytic material is able dissociate hydrocarbons without an applied varying potential, although it requires a higher temperature than is needed with porous silicon carbide. By covering only part of the porous surface 47 with the pad 52, there is still plenty of area of porous silicon carbide to adsorb hydrocarbon gases. If the device is operated at a low temperature (i.e., 100°–400° C.), the signal developed will be primarily due to dissociation of hydrocarbons in the porous silicon carbide 48 and will be dependent upon the applied varying potential. At a higher temperature (i.e.

>500° C.), the signal will also come from the catalytic dissociation of hydrocarbons in the pad 52.

By switching the varying potential on and off it is possible to determine how much of the signal is provided by the catalytic pad 52 (i.e., with the voltage off only the catalytic pad contributes to the final signal). At the same time, sweeping the varying potential can give some information about the type of hydrocarbon being dissociated. The efficiency of catalysis varies, to some extent, with the type of hydrocarbon and the type of catalytic material. Therefore, it is also possible to obtain more information about the species of hydrocarbons present by carefully selecting the catalytic material of the pad 52.

FIG. 7b shows an alternative organization that also employs the catalytic pad 52. Here the porous silicon carbide surface 47 has been etched away before the deposition of the pad 52. This removes possible attenuation of the catalytic signal by intervening porous silicon carbide layer 47 which has a very high electrical resistivity.

Figure 8:
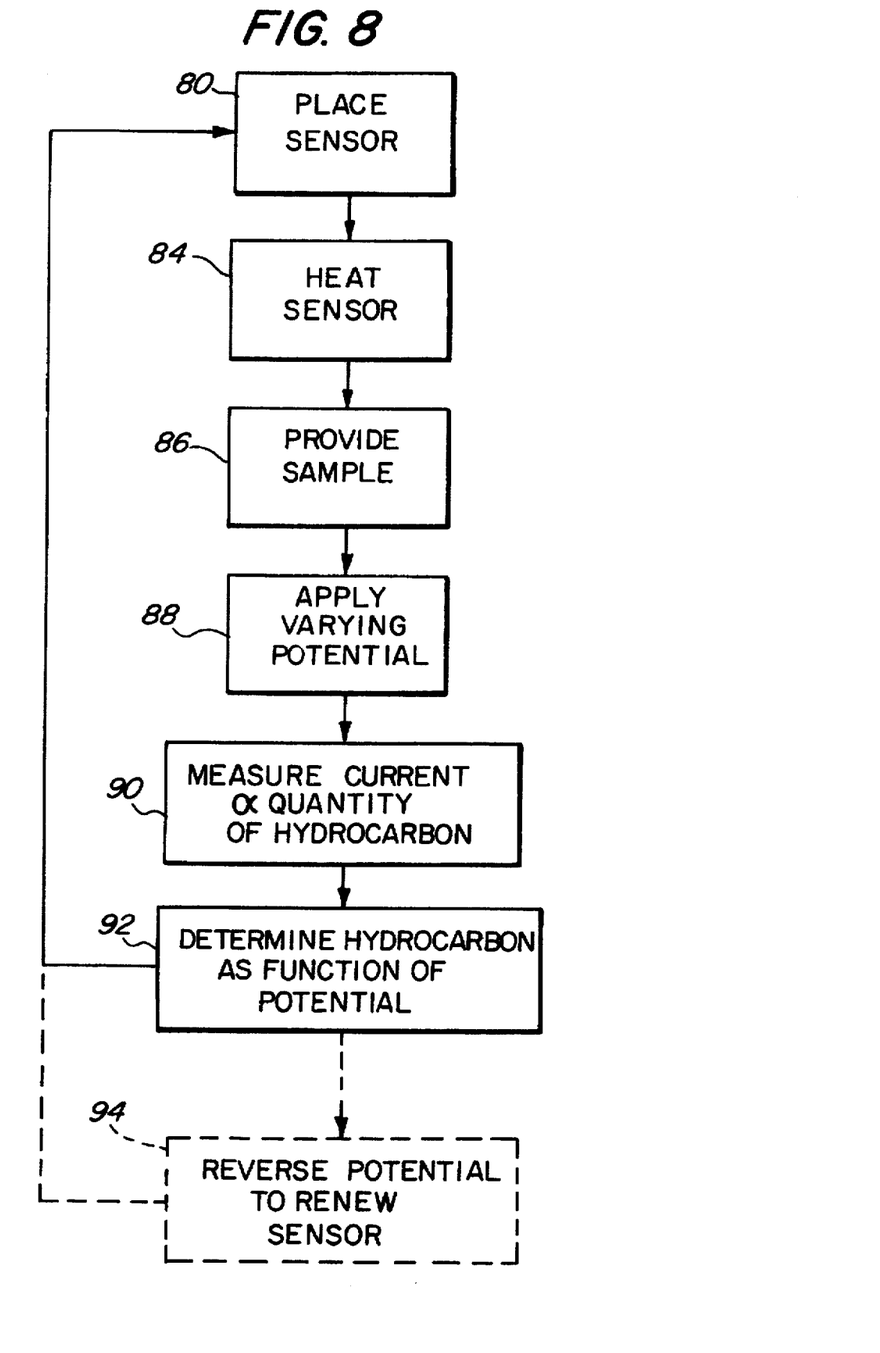
FIG. 8 shows a flow chart of the process of using the present invention.

FIG. 8 is a flow chart detailing the method of employing the devices of the present invention to detect the presence of hydrocarbon gases in an exhaust stream or other such milieu. A first step 80 is to place a device of the present invention in a location to measure a gas sample. The usual position is to mount the sensor, in an exhaust gas stream such as in the exhaust manifold of an automobile engine. Proper mounting hardware and high temperature electronic leads are required but are well known and do not form part of the present invention. The device used can be any of the MISFETs or MIS capacitors disclosed above. Since the transistors provide built-in amplification, they require less complex detection electronics and are preferred for most installations.

The next step 84 is to heat the device to operating temperature in excess of 100° C. and generally in excess of 200° C. Below the lower temperature the dissociation reactions are generally insufficiently rapid to provide an adequate signal. The catalytic reactions on the catalytic pad 52, if one is employed, are most effective above about 500° C. The transistors can operate up to at least 650° C., but at significantly higher temperatures there may be problems with etching or other damage to the sensor. In most cases the stream of gases to be analyzed is hot from the combustion process and provides the necessary heat. In the case of cooler gas streams a special heater such as an electric resistance heater can be supplied to heat the sensor to the proper temperature.

A sample gas is provided at the next step 86. The sample may be provided by placing the sensor in an exhaust stream. Alternatively the sensor may be in a special chamber and part of a gas stream may be diverted to the sensor, or the sensor may be inserted into a stationary gas sample in a container.

Application of a varying electrical potential to the sensor comprises the next step 88. As explained above, the various dissociation processes depend on a potential between 0 and about 10 V. Generally, it is convenient to sweep the potential over this range taking care that the rate of voltage change does not exceed the response rate of the sensor (response rate is influenced by the type of silicon, polycrystalline versus porous, thickness of the various device layers, concentration of detected gas, and temperature of the detection as well as other factors). Alternatively, if the chemical identity of the gases is known, the voltage can be swept over a more narrow range that includes the potentials of the known chemicals or the voltage can be switched between a number of discrete levels. In the case of sensors employing catalytic pads 52, it may be advantageous to include time periods where the varying potential is entirely switched off so that the output signal is indicative of the catalytic reaction only.

Step 90 comprises measuring an electrical characteristic that reflects binding and dissociation of hydrocarbons in the silicon carbide detection layer. In the case of transistor devices this would represent a change in the amount of current passing through the device from the source electrode 22 to the drain electrode 24. In the case of capacitor devices this would represent either a change in capacitor voltage measured by subjecting the capacitor to a higher frequency signal supplied in addition to the more slowly changing varying potential or a change in a current measured between the variable potential electrode 28 and the back electrode 46.

In step 92 the electrical characteristic change is correlated with the potential at which it occurs to identify the type of hydrocarbon present. As explained above, electrochemical reactions occur mostly between 0.3 V and 2-3 V, while dissociations occur mostly between 2 V and about 10 V. Individual chemical compounds tend to fall at slightly different potentials. Where both dissociation and electrochemical oxidation occurs, comparison of the potential for each type of reaction may identify a given chemical species. In other cases, comparison of a catalytic signal with a varying potential signal may identify the chemical species being measured.

The final optional step 94 is the application of a reverse potential to regenerate the sensor by helping to drive off reaction products and attracted impurities. Generally, the regenerating potential is about equal to the maximum dissociation potential (10 V) but is of an opposite polarity. In some cases a higher regeneration potential (i.e., up to about 100 V) gives improved regeneration. There is also some advantage to applying the dissociating potential as a continuously varying potential that sweeps from one extreme (say 10 V) to the opposite extreme (−10 V). In this way the device is regenerated constantly.

Those skilled in the art will appreciate that various adaptations and modifications of the just-described preferred embodiment can be configured without departing from the scope and spirit of the invention. Therefore, it is to be understood that, within the scope of the appended claims, the invention may be practiced other than as specifically described herein.

We claim:

1. An electronic device of semiconductor design for detecting hydrocarbon gases comprising:
    a detection layer having first and second surfaces, and forming a gate of a metal insulator field effect transistor, the detection layer comprising:
    a wafer of silicon carbide;
    a layer of porous silicon carbide formed at a first surface of said silicon carbide wafer by photoelectrochemical etching, the layer of porous silicon carbide for adsorbing hydrocarbon gases;
    a metal grid deposited onto the porous silicon carbide layer; and
    an electrode in electrical communication with the metal grid for applying a varying dissociating potential to said porous silicon carbide layer for dissociating hydrocarbon molecules adsorbed to said porous silicon carbide layer;
    an insulation layer formed on a second surface of the detection layer;
    a channel layer of doped silicon carbide formed on an exposed surface of the insulation layer; and drain and source electrodes disposed on the channel layer at opposite sides thereof so that dissociation of hydrocarbons in the detection layer causes an alteration in a current flow between the drain electrode and the source electrode, a magnitude of said alteration indicating a quantity of hydrocarbon gas adsorbed to the detection layer and a magnitude of the dissociating potential indicating a type of hydrocarbon gas adsorbed to the detection layer.

2. The electronic device of claim 1, wherein the wafer of silicon carbide forming the detection layer is hexagonal form silicon carbide fabricated with its C-axis normal to the first surface of said silicon carbide wafer.

3. The electronic device of claim 1, wherein the dissociating potential varies between 0 V and about 10 V.

4. The electronic device of claim 1, wherein the insulation layer comprises a layer of single crystal aluminum nitride.

5. The electronic device of claim 1, wherein the detection layer further comprises a layer of catalytic material deposited over an portion of the first surface of the porous silicon carbide layer.

6. The electronic device of claim 5, wherein the catalytic material is selected from the group consisting of platinum, vanadium, molybdenum carbide, tungsten carbide, titanium carbide, niobium carbide and palladium.

7. The electronic device of claim 5, wherein a region of the porous silicon layer is removed beneath the catalytic material so that the layer of catalytic material contacts the silicon carbide wafer.

8. An electronic device of semiconductor design for detecting hydrocarbon gases comprising:
 a detection layer having first and second surfaces, comprising:
  a region of porous silicon carbide formed at a first surface of said silicon carbide wafer by photoelectrochemical etching, the region of porous silicon carbide for adsorbing hydrocarbon gases;
  a metal grid deposited on the porous silicon carbide region; and
  a first electrode in electrical communication with the metal grid for applying
 a varying dissociating potential to said porous silicon carbide region for dissociating hydrocarbon molecules adsorbed to said porous silicon carbide region; and
 a second electrode deposited on a second surface of the silicon carbide wafer, the second electrode for applying a potential to said porous silicon carbide region in concert with the first electrode and for measuring changes of a current flow between the electrodes, a magnitude of the current flow indicating a quantity of hydrocarbon adsorbed to said porous silicon region and a magnitude of the dissociating potential indicating a type of hydrocarbon adsorbed to said porous silicon region.

9. The electronic device of claim 8, wherein the dissociating potential varies between 0 V and about 10 V.

10. The electronic device of claim 8, wherein the silicon carbide wafer forming the detection layer is hexagonal form silicon carbide with the C-axis normal to the first surface.

11. The electronic device of claim 8, wherein the detection layer further comprises a layer of catalytic material deposited over a portion of the porous silicon carbide region.

12. The electronic device of claim 11, wherein the catalytic-material is selected from the group consisting of platinum, vanadium, molybdenum carbide, tungsten carbide, titanium carbide, niobium carbide and palladium.

13. The electronic device of claim 11, wherein an area of the porous silicon layer is removed beneath the layer of catalytic material so that the layer of catalytic material contacts the silicon carbide wafer.

14. An electronic device of semiconductor design for detecting hydrocarbon gases comprising:
 a wafer of silicon carbide;
 a channel layer of doped silicon carbide formed on an exposed surface of the wafer with metallic drain and source electrodes disposed on the channel layer at opposite sides thereof; and
 an insulation layer formed on an exposed surface of the channel layer;
 a detection layer having a first and second surface, and forming a gate of a field effect transistor, the detection layer comprising:
  a layer of polycrystalline silicon carbide formed on an exposed surface of said insulation layer for adsorbing hydrocarbon gases;
  a metal grid deposited on the polycrystalline silicon carbide layer; and
  an electrode in electrical communication with the metal grid for applying a varying dissociating potential to said polycrystalline silicon carbide layer for dissociating hydrocarbon gas molecules adsorbed to the polycrystalline silicon carbide layer so that dissociation of hydrocarbon gas molecules causes an alteration in a current flow between the drain electrode and the source electrode, a magnitude of said alteration indicating a quantity of hydrocarbon gas adsorbed to the detection layer and a magnitude of the dissociating potential indicating a type of hydrocarbon gas absorbed to the detection layer.

15. The electronic device of claim 14, wherein the dissociating potential varies between 0 V and about 10 V.

16. The electronic device of claim 14, wherein the silicon carbide wafer is hexagonal form silicon carbide.

17. The electronic device of claim 14, wherein the silicon carbide wafer is cubic form silicon carbide.

18. The electronic device of claim 14, wherein the insulation layer comprises a layer of single crystal aluminum nitride.

19. The electronic device of claim 14, wherein the detection layer further comprises a layer of catalytic material deposited over a portion of the poly-crystalline silicon carbide layer.

20. An electronic device of semiconductor design for detecting hydrocarbon gases comprising:
 a detection layer with a first surface and a second surface, comprising:
  a wafer of silicon carbide;
  a layer of polycrystalline silicon carbide formed on a first surface of said wafer for adsorbing hydrocarbon gases;
  a metal grid deposited on the polycrystalline silicon carbide layer; and
  an electrode in electrical communication with the metal grid for applying a varying dissociating potential to said polycrystalline silicon carbide region, said dissociating potential for dissociating hydrocarbon gases adsorbed to the detection layer;
 an insulation layer formed on a second surface of the silicon carbide wafer; and
 a second electrode deposited on the insulation layer, the second electrode for applying a potential to said polycrystalline silicon carbide layer in concert with the first electrode and for measuring changes of current flow between the electrodes, a magnitude of the current flow indicating a quantity of hydrocarbon adsorbed to said polycrystalline silicon carbide layer and a magnitude of the dissociating potential indicating a type of hydrocarbon adsorbed to said polycrystalline silicon carbide layer.

21. The electronic device of claim 20, wherein the dissociating potential varies between 0 V and about 10 V.

22. The electronic device of claim 20, wherein the detection layer further comprises a layer of catalytic material deposited over an area of the poly-crystalline silicon carbide layer.

23. A method of employing a semiconductor device to detect hydrocarbon gases comprising the steps of:

providing a semiconductor device with a detection layer of silicon carbide to interact with a gas sample;

operating said semiconductor device at temperatures between about 100° C. and 650° C.;

introducing a gas sample to be tested by exposure to a surface of the detection layer so that the gas sample adsorbs to the detection layer;

varying a dissociating potential applied to the detection layer;

measuring a change in an electrical characteristic of the semiconductor device as indicative of a quantity of hydrocarbon gas adsorbed to the detection layer; and measuring the potential at which the change in an electrical characteristic occurs as indicative of a type of hydrocarbon gas present in the detection layer.

24. The method of claim 23, wherein the detection layer further comprises a pad of catalytic material covering a portion of the silicon carbide of the detection layer.

25. The method of claim 24, wherein the catalytic material is selected from the group consisting of platinum, vanadium, molybdenum carbide, tungsten carbide, titanium carbide, niobium carbide and palladium.

26. The method of claim 23, wherein the dissociating potential is varied between about 0 V and 10 V.

27. The method of claim 23 further comprising a step of reversing polarity of the dissociating potential to regenerate the semiconductor device.

\* \* \* \* \*